United States Patent [19]

Del Val et al.

[11] Patent Number: 4,828,992
[45] Date of Patent: May 9, 1989

[54] PROCESS FOR THE MANUFACTURE OF AN ANTIFUNGAL ANTIHYPERCHOLESTEROLEMIC β-LACTONE

[75] Inventors: Sagrario M. Del Val; Maria I. M. Fernandez, both of Madrid, Spain; Richard L. Monaghan, Somerset, N.J.

[73] Assignee: Merck & Co., Inc., Rahway, N.J.

[21] Appl. No.: 825,497

[22] Filed: Feb. 3, 1986

[51] Int. Cl.$^4$ .................. C12P 17/02; C12P 7/40; C12N 1/14; C12R 1/77
[52] U.S. Cl. .................. 435/123; 435/254; 435/136; 435/929; 435/142
[58] Field of Search ............ 435/929, 911, 254, 123, 435/136, 142

[56] References Cited

U.S. PATENT DOCUMENTS 3,546,073 12/1970 Evans et al. .................. 435/929

OTHER PUBLICATIONS

Turner, Fungal Metabolites, Academic Press, 1971, pp. 351–359.

Turner et al., Fungal Metabolites II, Academic Press, 1983, pp. V–VII and 467–476.
Aldridge et al., "Antibiotic 1233A: a Fungal Beta-Lactone", *J. Chem. Soc. (C)*, 1971, vol. 23, pp. 3888–3891.

*Primary Examiner*—Charles F. Warren
*Assistant Examiner*—Irene Marx
*Attorney, Agent, or Firm*—Melvin Winokur; Joseph F. DiPrima

[57] ABSTRACT

The process for the manufacture of the compound of the general structural formula

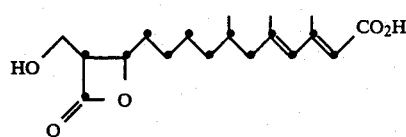

which is a 3-hydroxy-3-methylglutarylcoenzyme A (HMG-CoA) synthase inhibitor and useful as an antihypercholesterolemic agent for the treatment of disease in which the inhibition of cholesterol biosynthesis would be useful, and which is an antifungal agent is disclosed.

8 Claims, No Drawings

PROCESS FOR THE MANUFACTURE OF AN ANTIFUNGAL ANTIHYPERCHOLESTEROLEMIC β-LACTONE

BACKGROUND OF THE INVENTION

The compound, 12-hydroxy-13-hydroxymethyl-3,5,7-trimethyltetradeca-2,4-dien-1,14-dioic acid 12,14-lactone, was identified as an antibiotic fungal metabolite in 1970 [Aldridge et al., Chem. Comm., 1970, p. 639]. This compound has also been found to have antifungal and antihypercholesterolemic properties as described in co-pending application Ser. No. 825,496 filed contemporaneously herewith and co-pending application Ser. No. 822,501 Jan. 27, 1986 filed previously.

SUMMARY OF THE INVENTION

This invention relates to the novel process for the preparation of the compound, 12-hydroxy-13-hydroxymethyl-3,5,7-trimethyltetradeca-2,4-dien-1,14-dioic acid, 12,14-lactone, by the cultivation of a member of the class of fungi selected from ATCC 20788, ATCC 20789 or ATCC 20790 followed by a standard isolation. A culture of the above noted strains has been deposited in the American Type Culture Collection, Rockville, Md. as type culture under the respective accession numbers.

DETAILED DESCRIPTION OF THE INVENTION

The morphological characteristics of the microorganisms ATCC 20788, ATC 20789 and ATCC 20790 are described below:

Fusarium sp. MF5045 ATCC 20788

Cultural Characteristics

On Czapek-Dox agar - mycelia is extensive, white and cottony, becoming felted and white with sectors of faint bluish-green tinge or a pale peach tinge as culture ages. Moist areas faint bluish-green in color develop where macroconidia are abundant.

On potato-dextrose agar - mycelia is extensive, white and cottony, becoming felted and pinkish-tan in color as culture ages. When vegetative incoculum is used, moist areas, tan in color, develop where macroconidia are abundant.

On Sabouraud-maltose agar - mycelia is extensive, velvety and white with peach to light purple tinge.

Morphological Characteristics

Microconidia are generally unicellular, oval-ellipsoidal, borne singly and held in a gelatinous mass. $1.8-2.4\mu \times 3.6$ to $4.8\mu$.

Macroconidia are 3 to 5 celled, thin-walled, ends are tapered and slightly curved. $3.6-4.8\mu \times 24-36\mu$.

Chlamydospores are abundant, terminal and intercalary, globose, generally smooth-walled, usually formed singly but sometimes formed in pairs.

Fusarium sp. MF5058 ATCC 20789

Cultural Characteristics

On Czapek-Dox agar - mycelia is extensive, white and cottony, becoming felted and white with sectors of a faint bluish-green tinge or a pale peach tinge as culture ages. Moist areas faint bluish-green in color develop where macroconidia are abundant.

On potato-dextrose agar - mycelia is extensive, white and cottony, becoming felted and pinkish-tan in color as culture ages. When vegetative inoculum is used, moist areas, tan in color develop where macroconidia are abundant.

On Sabouraud-maltose agar - mycelia is extensive, velvety and white with peach to light purple tinge.

Morphological Characteristics

Microconidia are generally unicellular, oval-ellipsoidal, borne singly and held in a gelatinous mass. $1.8-2.4\mu \times 3.6-4.8\mu$.

Macronconidia are 3 to 5 celled, thin-walled, ends are tapered and slightly curved $3.6-4.8\mu \times 24-36\mu$.

Chlamydospores are abundant, terminal and intercalary, globose, generally smooth-walled, usually formed singly but sometimes formed in pairs.

Fusarium sp. MF 5084 ATCC 20790

Cultural Characteristics

On Czapek-Dox agar - mycelia is extensive, white and cottony, becoming felted and white with sectors of a faint bluish-green tinge or a pale peach tinge as culture ages. Moist areas faint bluish-green in color develop where macroconidia are abundant.

On potato-dextrose agar - mycelia is extensive, white and cottony, becoming felted and pinkish-tan in color as culture ages. When vegetative inoculum is used, moist areas, tan in color, develop where macroconidia are abundant.

On Sabouraud-maltose agar - mycelia is extensive, velvety and deep-pinkish tan in color. Vegetative growth and medium become purplish-red.

Morphological Characteristics

Microconidia are generally unicellular, oval-elliposoidal, borne singly and held in a gelatinous mass $1.8-2.4\mu \times 3.6-4.8\mu$.

Macroconidia are 3 to 5 celled, thin-walled, ends are tapered and slightly curved. $3.6-4.8\mu \times 24-36\mu$.

Chlamydospores are abundant, terminal and intercalary, globose, generally smoothed-walled formed singly but sometime formed in pairs.

The compound, 12-hydroxy-13-hydroxymethyl-3,5,7-trimethyltetradeca-2,4-dien-1,14-dioic acid 12,14-lactone, is produced by the cultivation of a member of the class of fungi ATCC 20788, ATCC 20789, or ATCC 20790 under the following general conditions.

A preserved source of the culture is used to inoculate an agar slant containing a nutrient medium for growth. After incubation at room temperature for 1 to 5 weeks a portion of this growth is used to inoculate a liquid nutrient medium containing sources of carbon, nitrogen, phosphorus and other elements necessary for life. This medium is incubated at 25° to 30° C., usually 28°. The flask containing the culture and liquid nutrient medium is incubated with or without agitation on a rotary shaker from 0 to 400 RPM, most often at 212 RPM. After 1 to 10 days, when growth is abundant, usually between 2 and 4 days, the culture growth is used to inoculate a flask containing a medium which supports production of the product. Such production media contain carbon sources such as corn, glycerol, corn oil, dextrose, cod oil or peanut meal, nitrogen and sulfur sources such as yeast extract, corn steep liquor, corn, lard water, peanut meal, soy flour, tomato paste and the like as well as organic and inorganic ions such as potassium, phosphorous, calcium, tartrate, iron and magnesium. These production media are inoculated with the culture growth and are incubated at from 20° to 30° most often 25° for 3 to 30 days usually 7-14 days with or without agitation.

The compound may be recovered from the fermentation medium by extration with a water miscible solvent, such as $C_{1-3}$ alcohol, especially methanol and water in a ratio from 0.1:1.0 to 1.0 to 0.1, especially 1:1 by volume. The extract is partioned between the aqueous phase and a water miscible organic solvent such as ethyl acetate or methylene chloride. The desired compound is further purified by chromatography on silica gel and then Sephadex LH20 (tradename for dextran derivatives used as gel filtrants in organic solvents, manufactured by Pharmacia Fine Chemicals, Inc.). Finally, the product may be crystallized from aqueous alcohol.

The following example illustrates the preparation of the compound and as such are not to be construed as limiting the invention set forth in the claims appended hereto.

The composition of media employed in the following examples are listed below. Media are prepared in a 250 ml Erlenmeyer flask. The contents are sterilized with steam at 121° C., 20 pounds pressure for 20 minutes. Media that contain corn are rehydrated and again sterilized with steam at 121° C., 20 pounds pressure for 20 minutes before inoculation.

F867: 10 g/flask corn, 0.1 g/flask $MgSO_4.7H_2O$, 0.01 g/flask $FeSO_4.7H_2O$, 15 ml/flask of (33 g/l yeast extract) after 7 days incubation add 20 ml $H_2O$/flask, incubate without agitation for 14 days F870: 10 g/flask corn, 0.01 g/flask $FeSO_4.7H_2O$, 0.01 g/flask $ZnSO_4.7H_2O$, 15 ml/flask of (33 g/l yeast extract), incubate without agitation for 14 days F872: 10 g/flask corn, 15 ml/flask of (33 g/l yeast extract) incubate without agitation for 7 days then at 220 rpm for 7 days F848: 10 g/flask corn, 15 ml/flask of ($MgSO_4.7H_2O$ 0.1 g/l, Na tartrate 0.1 g/l, $FeSO_4.7H_2O$ 0.01 g/l, $ZnSO_4.7H_2O$ 0.01 g/l) incubate at 220 rpm for 7 days

| | |
|---|---|
| Corn Steep | 5 g |
| Tomato Paste | 40 g |
| Oat Flour | 10 g |
| Dextrose | 10 g |
| Distilled water | 1000 ml |
| Trace Element Mix No. 2-10 ml of ($FeSO_4.7H_2O$ 1g/l, $MnSO_4.4H_2O$ 1g/l, $CuCl_2.2H_2O$ 25 mg/l, $CaCl_2.2H_2O$ 100 mg/l, $H_3BO_3$ 56 mg/l, $(NH_4)_6Mo_7O_{24}.4H_2O$ 19 mg/l, $ZnSO_4.7H_2O$ 200 mg/l, Deionized water 1000 ml) pH 6.8 | |
| Yeast extract | 4 g |
| Malt extract | 10 g |
| Dextrose | 4 g |
| Agar | 20 g |
| pH 7 | |
| Distilled water | 1000 ml |

EXAMPLE 1

Preparation of 12-Hydroxy-13-hydroxymethyl-3,5,7-trimethyltetradeca-2,4-dien-1,14-dioic acid 12,14 lactone (a) Fermentation of ATCC 20790.

A culture of ATCC 20790 was inoculated onto YME slant medium. After growth at 25° C., a portion of this slant was used to inoculate a baffled 250 ml Erlenmeyer flask containing KF growth medium (54 ml). The flask was incubated with agitation at 212 rpm on a rotary shaker (2 inch throw) for 3 days at 28° C. Then a portion of the growth (2 ml) was used to inoculate an unbaffled 250 ml Erlenmeyer flask containing Medium F867 (media F870 or F872 may also be employed). After 14 days incubation at 25° C. methanol (20 ml) was added and then let stand overnight. Then water (10 ml) was added to the flask. The desired product was contained in the aqueous methanol extract.

(b) Fermentation of ATCC 20789.

(1) A preserved culture source of ATCC 20789 was used to inoculate a baffled 250 ml Erlenmeyer containing KF growth medium (54 ml). The flask was incubated with agitation at 212 rpm on a rotary shaker (2 inch throw) for 3 days at 28° C. Then a portion of the growth (2 ml) was used to inoculate an unbaffled 250 ml Erlenmeyer flask containing medium F870. After 14 days incubation at 25° C., 50 percent aqueous methanol was added. The aqueous methanol extract was employed in the isolation and purification procedure described below.

(c) Fermentation of ATCC 20788.

A culture of ATCC 20788 was used to inoculate a baffled 250 ml Erlenmeyer flask containing KF growth medium (54 ml). The flask was incubated with agitation at 212 rpm on a rotary shaker (2 inch throw) for 3 days at 28° C. Then a portion of the growth (2 ml) and remaining medium was used to inoculate an unbaffled 250 ml Erlenmeyer flask containing medium F848. After 7 days incubation at 25° C., the contents of the flask were extracted with methanol (20 ml) in water (10 ml) to obtain the desired product.

(d) Isolation and Purification

The aqueous methanol extracts (700 ml each) from the fermentation medium from two series of fermentations of the microorganism ATCC 20789 according to the general procedure of Example 1(b) were filtered. The first extract was partitioned with methylene chloride (700 ml) and the second extract was partitioned with ethyl acetate (700 ml). In both cases activity was located in the organic phase. The two organic phases were combined and concentrated in vacuo. The residue was dissolved in ethyl acetate/hexane (4:6) (2 ml) and chromatographed on silica gel (200 ml) eluted with a step gradient of ethyl acetate:hexane (4:6, 6:4, 5:5 and 7:3). The desired product was rechromatographed on LH-20 (20 ml) eluted with methylene chloride:hexane: methanol (10:10:1) and the desired product eluted from the column with methanol. An analytically pure sample of the title compound was a crystalline compound mp. 76°–77° C.

The $^{13}C$ NMR spectrum was recorded in $CD_3OD$ at ambient room temperature (25 mg/0.4 ml) on a Varian XL 400. Chemical shifts are given in ppm downfield of tetramethylsilane relative to the solvent peak at 49.0 ppm as standard. In agreement with the mass spectral data, 18 carbon atoms are observed with the following chemical shifts: 18.5, 19.8 (2×), 26.4, 27.8, 32.0, 35.0, 37.8, 49.9, 58.0, 60.0, 76.3, 118.7, 130.6, 142.3, 155.7, 170.4, 171.9 ppm.

Mass Spectrum Calc'd for $C_{18}H_{28}O_5+H$: 325.2015. Found: 325.2015.

What is claimed is:

1. A process for the manufacture of an antifungal antihypercholesterolemic compound represented by the formula

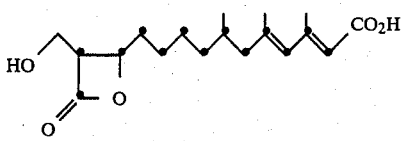

which comprises culturing a microorganism selected from the group consisting of Fusarium sp ATCC 20788, ATCC 20789 and ATCC 20790 in a semi-solid nutrient medium containing assimilable sources of nitrogen and carbon under aerobic condition until a substantial amount of the compound is produced and isolating the compound so produced.

2. A process of claim 1 in which the microorganism is ATCC 20788.

3. A process of claim 1 in which the microorganism is ATCC 20789.

4. A process of claim 1 in which the microorganism is ATCC 20790.

5. A process of claim 1 in which the culturing of the microorganism occurs at a temperature between 22° and 28° C.

6. A process of claim 5 in which the temperature is 25° C.

7. A process of claim 1 in which the culturing of the microorganism continues from 7 days to 14 days.

8. A biologically pure culture of a microorganism selected from the group consisting of Fusarium sp. MF 5045 (ATCC 20788), Fusarium sp. MF 5058 (ATCC 20789) and Fusarium sp. MF5084 (ATCC 20790), said microorganism being capable of producing 12-hydroxy-13-hydroxymethyl-3,5,7-trimethyltetradeca-2,4-dien-1,14-dioic acid 12,14-lactone in recoverable quantity upon cultivation in a nutrient medium containing assimilable sources of nitrogen and carbon under aerobic conditions.

* * * * *